(12) United States Patent
Naylor

(10) Patent No.: US 7,878,112 B2
(45) Date of Patent: Feb. 1, 2011

(54) APPARATUS AND METHODS FOR STORING SENSITIVE MATERIALS

(75) Inventor: Stuart Naylor, Surrey (GB)

(73) Assignee: Roylan Developments Limited, Surrey (GB)

( * ) Notice: Subject to any disclaimer, the term of this patent is extended or adjusted under 35 U.S.C. 154(b) by 721 days.

(21) Appl. No.: 11/883,296

(22) PCT Filed: Jan. 30, 2006

(86) PCT No.: PCT/GB2006/000307

§ 371 (c)(1),
(2), (4) Date: Jul. 30, 2007

(87) PCT Pub. No.: WO2006/095121

PCT Pub. Date: Sep. 14, 2006

(65) Prior Publication Data

US 2008/0099348 A1     May 1, 2008

(30) Foreign Application Priority Data

Jan. 31, 2005    (GB) ................................ 0501904.7

(51) Int. Cl.
*A23L 1/00* (2006.01)
*A23L 3/34* (2006.01)

(52) U.S. Cl. ............................. 99/467; 99/468; 99/473; 426/231; 426/232; 426/418; 34/211; 34/218; 34/467; 34/516

(58) Field of Classification Search .................... 99/467, 99/473, 468; 426/419, 418, 415, 231, 232; 34/467, 516, 218, 211; 62/78, 239
See application file for complete search history.

(56) References Cited

U.S. PATENT DOCUMENTS 3,715,860 A    2/1973   Esty
4,344,467 A    8/1982   Lahde (Continued)

FOREIGN PATENT DOCUMENTS

DE      197 53 185 A1    6/1999

(Continued)

*Primary Examiner*—Reginald L Alexander
(74) *Attorney, Agent, or Firm*—Breiner & Breiner, LLC

(57) ABSTRACT

Apparatus is described for storing sensitive materials in containers (32) which are sealed and in which the internal atmosphere may be purged by flushing with an inert gas fed in from a purger unit (30) via a suitable feed lead (35). The gas exhausted from inside the container (32) is fed back into the purge unit (30) and then checked against a desired parameter, for example oxygen concentration, until the value of that parameter reaches a desired level. Purging may then be stopped and the container left sealed, preferably at a slight over pressure relative to the ambient atmosphere. The use of a separate purge unit enables many containers to be sequentially and effectively processed. The containers are particularly useful for storing sensitive chemical and biological samples.

11 Claims, 3 Drawing Sheets

U.S. PATENT DOCUMENTS

| | | | |
|---|---|---|---|
| 4,707,953 A | | 11/1987 | Anderson et al. |
| 4,961,322 A | * | 10/1990 | Oguma et al. ............. 62/179 |
| 5,355,781 A | * | 10/1994 | Liston et al. ............. 99/476 |
| 5,794,408 A | | 8/1998 | Patouraux et al. |
| 5,799,495 A | * | 9/1998 | Gast et al. ............. 62/78 |
| 5,960,708 A | | 10/1999 | DeTemple et al. |
| 6,013,293 A | * | 1/2000 | De Moor ............. 426/106 |
| 6,023,915 A | | 2/2000 | Columbo |
| 6,113,671 A | | 9/2000 | Garrett |
| 6,230,614 B1 | * | 5/2001 | Del Gallo et al. ............. 99/467 |
| 7,650,835 B2 | * | 1/2010 | Stein ............. 99/468 |
| 2001/0041530 A1 | | 11/2001 | Hara |
| 2002/0177749 A1 | | 11/2002 | Brown |
| 2003/0150334 A1 | * | 8/2003 | Gbler ............. 99/325 |
| 2004/0101606 A1 | * | 5/2004 | Ling et al. ............. 426/419 |
| 2004/0262187 A1 | | 12/2004 | Schauer |

FOREIGN PATENT DOCUMENTS

| | | |
|---|---|---|
| EP | 0 544 075 A1 | 6/1993 |
| GB | 2 271 439 A | 4/1994 |
| JP | 02-242771 A | 9/1990 |
| WO | WO 99/35054 A1 | 7/1999 |

\* cited by examiner

APPARATUS AND METHODS FOR STORING SENSITIVE MATERIALS

This application relates to apparatus and methods for storing sensitive materials. In particular, it relates to systems in which sensitive materials are stored in a plurality of containers, each of which may constitute a sealed enclosure preventing the exchange of physical material between the external surroundings of the container, normally the ambient atmosphere, and the contents of the container. The contents are the sensitive material itself together with an appropriate atmosphere. The container may also include, for example, means for supporting the sensitive material itself.

U.S. Pat. No. 5,855,272 discloses a system of storing sensitive materials, in this particular case audio or audio-visual recordings, by placing them in an hermetically sealable container and purging the interior of the container with an inert gas such as nitrogen or argon. Following such purging the lid of the container may be finally closed to seal it and extra purge gas injected to render the pressure of the atmosphere in the interior of the container positive with respect to ambient, thus ensuring that any leakage, at least initially, transfers material from the inside of the container to the outside rather than letting anything from the outside in.

U.S. Pat. No. 5,561,915 discloses a container with an inbuilt carbon dioxide cartridge chamber. After the container is sealed, a cartridge is inserted into the chamber and acts to inject carbon dioxide into the interior, displacing the atmosphere therein which is exhausted via an exhaust orifice. After the atmosphere inside the container has been replaced with carbon dioxide, the spent cartridge is disposed of and the exhaust orifice sealed with a pipe plug.

A particular storage problem arises in the pharmaceutical and biotech industries in connection with the transportation and storage of sample materials. Particularly biotechnological materials tend to be unstable and need to be carefully handled. Not only must care be taken not to allow samples to be contaminated by dust, but it is desirable that they are protected from adverse effects from heat sources, light, or exposure to reactive materials such as oxygen or moisture in the atmosphere.

One particular area of substantial concern is the preservation of the compounds used in pharmaceutical research. These are very often highly sensitive and are conventionally handled and stored as a solution of the compound concerned in dimethyl sulphoxide. This is a very strong solvent for a very wide range of organic compounds and one which does not interact chemically with them. On the other hand the material itself, dimethyl sulphoxide, is highly hydrophilic, and accordingly tends to absorb moisture from the ambient atmosphere which can then interact with the compound in solution in the dimethyl sulphoxide. Accordingly, it is highly desirable to preserve and store such materials even though the sensitive materials are already in solution, in a controlled non-interactive environment because the solution itself can be categorised as a sensitive material.

The present invention generally provides a system consisting of a plurality of portable containers for the storage of sensitive materials, each of which has an inlet port, an exhaust port, and means for sealing the interior of the container from the outside, together with a container interior conditioning apparatus in the form of apparatus adapted to inject an inert gas under pressure into one of the individual containers via the inlet port thereof, and to analyse and monitor the gas emerging from the exhaust port thereof, and adapted, on detection of a desired condition of the gas exhausted from the container, to discontinue injecting further gas via the inlet port.

The apparatus may include a gas analysis or detection system to monitor the content of the exhaust gas, for example an oxygen sensor to detect the oxygen concentration in that gas, or a moisture content sensor.

The apparatus preferably includes means to inject sufficient purge gas into the container to leave the container pressurised to assist in offsetting the adverse effect of any leakage of the seal. The degree to which it is pressurised may be chosen as desired, but is usually relatively small, particularly since if the pressure inside the sealed container is substantial relative to ambient pressure, there is not only a risk of the seal failing but additionally the sides of the container may bulge, so preventing clean stacking of a number of containers in a suitable storage facility.

Regulations concerning pressurised systems and pressure vessels may also need to be respected, though it is more usual simply to use the apparatus to pressurise the container only to an extent not covered by such regulations.

A preferred way of achieving the desired excess pressure in the container is to configure the purging apparatus so that after the purge gas has been injected sufficiently long for the exhaust gas to reach the acceptable condition, the pressure in the container is allowed to drop by venting gas from the interior of the container while measuring the pressure, and ceasing to vent gas once the desired excess pressure level is reached.

Although it is often simple and convenient to purge the atmosphere inside the containers or on a container by container basis, it is possible to operate in other ways. For example, it is possible to purge a set of containers connected in series, with the source of purge gas connected to the inlet port of the first container in the series, the outlet port of the first container in the series connected to the inlet port of the second, and so on, the outlet port of the last container in the series being connected to the purge gas apparatus. Obviously the purging process will then take considerably longer to flush all of the existing ambient atmosphere from the containers, but overall time advantages may be gained by that sort of batch processing. In a further alternative, the purge gas outlet from the gassing apparatus may be distributed via a manifold to a plurality of inlets on a plurality of containers essentially arranged in parallel, the exhaust ports for each of the containers being likewise connected to a manifold which then connects to the inlet port on the gassing apparatus.

The exact nature of the individual containers for sensitive products may vary widely, the fundamental requirements however being that the interior of the container may be sealed against the outside and that the container has an inlet port and outlet port. Within these constraints, the container may vary widely. It is convenient for many practical industrial applications to produce the containers in a number of standard sizes and the gassing apparatus may include a simple control to adjust the parameters such as gassing time, over-pressure and the like in accordance with the type and size of container in question.

A preferred mode of construction of the containers is that of an open-topped box with a lid, the walls of the box and the material of the lid being of gas-impermeable material, for example sheet metal. Clearly sealing means need to be provided to enable the lid to be sealed to the edges of the open-topped box. This may be, for example, a resilient rubber or rubber-like material seal around the inside angled corner of a generally tray-shaped lid, and means may be provided on the open-topped box to enable the lid to be firmly held against the top of the open-topped box to seal its interior against the ambient atmosphere. Alternatively, the upper edges of the walls of the box may carry an annular seal strip of U-shaped cross section and made of an appropriate resilient sealing material.

The inlet and outlet ports may be mounted on the walls of the box in customary sealed fashion. Preferably both ports are simple one-way or check valves. By providing that the exhaust port has an exhaust valve which opens only when the pressure within the container is above a preset level, the operation of purging the atmosphere from the interior of the container and then pressurising it may be rendered very straightforward.

The interior of the containers may be provided if desired with any convenient fittings to assist the storage operation envisaged. For example, the interior may be divided into a number of compartments, for example six compartments in a 3×2 array, into each of which a standard unit may be inserted. For example, in handling biological samples, standard size so-called plate or tube racks are widely used and the storage container may be sized and shaped to enable an array of such racks to be easily accommodated.

Preferably the inlet and outlet ports are standard pneumatic ports adapted for cooperating by a quick fit/quick release action with an appropriate fitting on the end of a tube such as a pressure line or exhaust line.

The purge gas used in practising the present invention is conventionally nitrogen because it is inexpensive and effective though, for certain high specification areas, argon may be used. There is, of course, no reason not to use any other appropriate inert purge gas.

The gassing apparatus may be constructed according to appropriate principles of engineering design and to suit the particular sensitive material storage problem envisaged. It will need to be provided with some form of power supply to operate and, of course, with a supply of purge gas, conveniently from a standard gas storage cylinder which may be connected to the gassing apparatus using conventional pressurised leads.

The invention is illustrated by way of example only with reference to the accompanying drawings in which.

Figure 1:
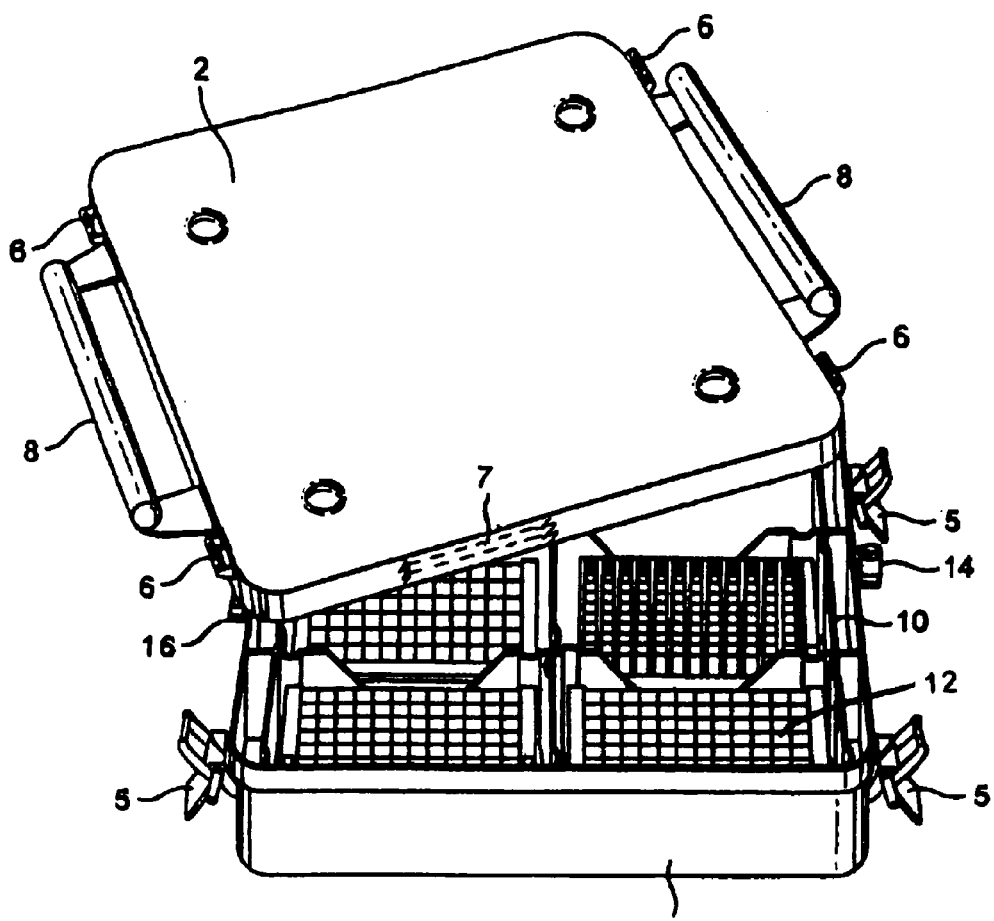
FIG. 1 is a perspective view of a storage container and lid for use in the present invention.

Referring to the drawings, FIG. 1 shows a container for use in practising the invention. It consists of a metal base section 1 and a metal lid 2 in the form of a plate having a depending skirt which is adapted to fit closely around the upper edge of the side wall of the base section 1. Mounted on the side of base section 1 are four standard clips 5, each of which has a portion adapted to engage over a tab 6 located on the skirt of lid 2 and thereby urge lid 2 down towards base section 1.

Shown in phantom lines in FIG. 1 is an internal annular seal 7 which runs round the inside of lid 2 and which is of an appropriate resilient material such as a rubber or silicone compound. It is in the form of an even thickness bead into which the top edge of the side walls of base section 1 is urged as the clips 5 pull the lid downwards via tabs 6.

Two carrying handles 8 are mounted on opposite sides of the skirt forming part of lid 2 so that once the base section 1 and the lid 2 are assembled and clipped together, the entire assembly can be lifted by handles 8.

As shown in the drawing, the interior of the base has a set of dividing walls 10 which may be a preformed structure which is a relatively loose fit in the base, and which divides the space within the base section 1 into six compartments, each of which may receive a standard size sample array 12.

Mounted on one wall of the base 1 is an inlet port 14 of conventional pneumatic construction. An exhaust port 16 is mounted on the opposite wall to port 14.

Figure 2:
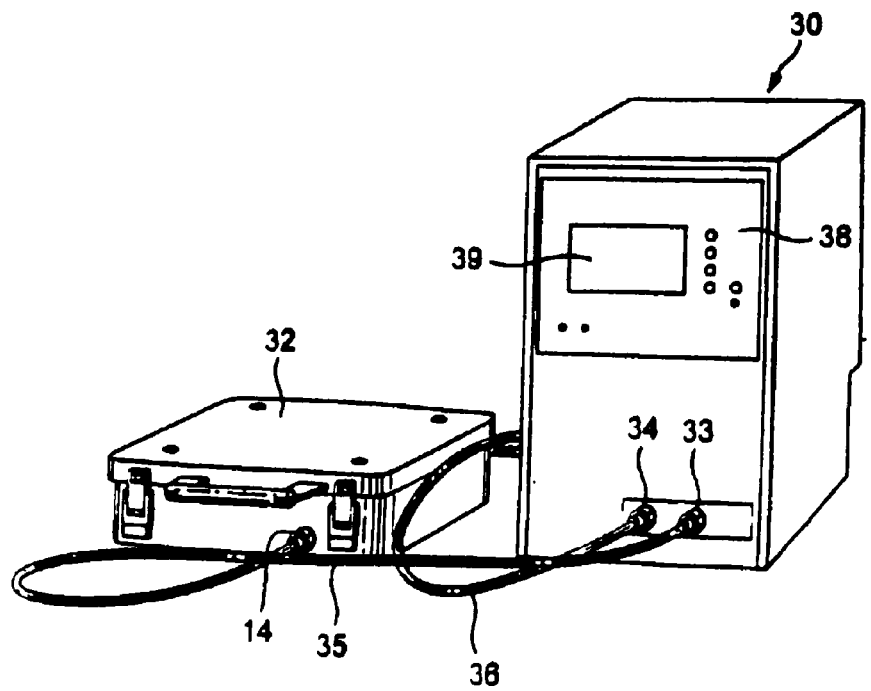
FIG. 2 is a perspective view of a typical gassing apparatus shown connected to a container of the type illustrated in FIG. 1.

FIG. 2 shows a typical arrangement of a system in accordance with the present invention. On the right is a purge gas unit generally denoted 30 the on the left a container of the type shown in FIG. 1 and generally denoted 32.

As can be seen, unit 30 consists of a generally rectangular casing having outlet and inlet ports 33 and 34 mounted on its front face. A pneumatic line 35 is connected between the outlet port 33 of the purge gas unit 30 and the inlet port 14 on container 32. A pneumatic line 36 connects the outlet port on container 32 with inlet port 34 on the unit 30.

Unit 30 also has a control panel 38 including a display screen 39. Not shown in FIG. 2 are an electrical supply connection to unit 30 (which may be a normal mains lead which can be plugged in to any suitable electricity supply socket) and a source of purge gas, preferably a standard gas cylinder with the usual pressure reduction outlet valve mounted at its top and connected to an inlet port at the rear of unit 30 via an appropriate pipe.

Figure 3:
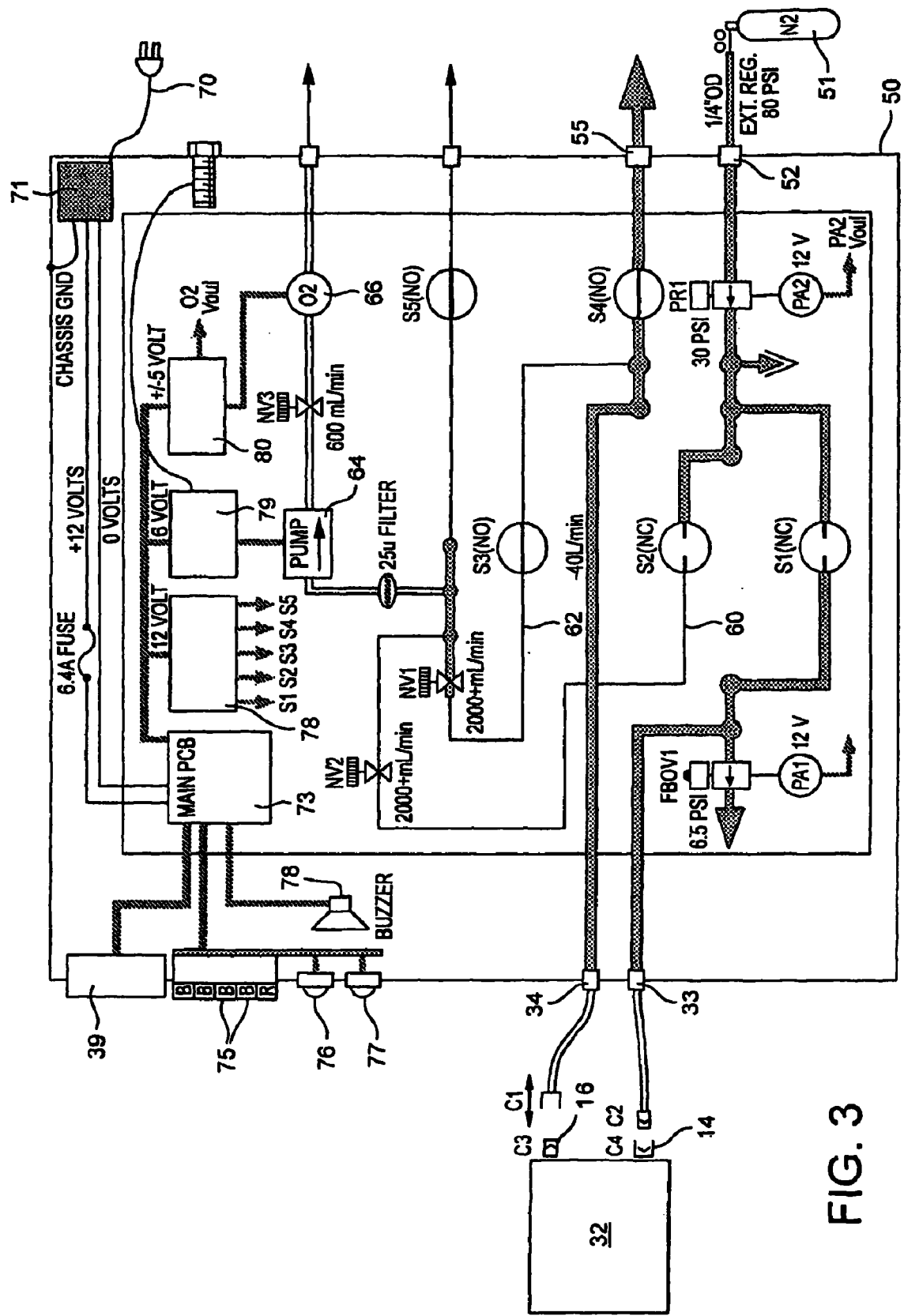
FIG. 3 is a diagram showing the internal pneumatic circuit and some associated electrical circuitry of the device shown in FIG. 2.

The pneumatic circuit of the unit 30 is shown in FIG. 3. Referring to this figure, this shows the internals of the unit 30 diagrammatically. The casing itself is denoted 50, and as can be seen the major purge gas flow runs in a generally clockwise direction as shown in FIG. 3 from a compressed nitrogen bottle 51 shown at the lower right hand corner via a standard high pressure lead and an inlet port 52 through a main feed line to the outlet port 33 mounted on the front of the unit 30 which is connected to the inlet port 14 of the container 32. The outlet port 16 of the container 32 is connected to the inlet port 34 on the front of the unit 30 and then passes through the unit 30 to a vent 55 located on the rear of the unit.

As can be seen in FIG. 3, branch lines 60 and 62 branch from the purge gas feed and exhaust and these may be selectively connected to the upstream side of a pump 64 which is in turn located upstream of an oxygen sensor unit through which gas may be passed, the downstream side of the sensor 66 being connected to a simple vent to atmosphere 68 located in the rear wall of the casing of unit 30.

The main purge gas feed lines contain at the positions shown five solenoid operated valves S1 to S5, each being denoted NC for a valve which is normally closed when no power is applied and NO for one which is usually open when no power is applied.

The interior of the case also includes electrical circuitry in particular for controlling the operation of the various solenoid valves and the pump 64, and which receives signals from appropriate pressure sensors and the oxygen sensor 66. Thus as shown in FIG. 3, a mains supply may be fed to the unit 32 using a normal power cord and plug arrangement 70 which is connected to a standard power supply unit 71 providing a 12 Volt output to drive the various electronic and electromechanical components. This is accomplished via the intermediation of a main circuit board 73 which is powered from power supply 71 and which is connected in appropriate fashion to the display 39, a set of programming buttons 75 which are accessible from the front of the unit 30, some indicator LEDs 76, 77 and an audio transducer 78. The main printed circuit board 73 is also connected to appropriate driver circuits generally indicated at 78 for the solenoid valves, to a driver circuit 79 for pump 64 and to supply the appropriate voltage to the oxygen sensor controller generally designated 80.

Figure 4:
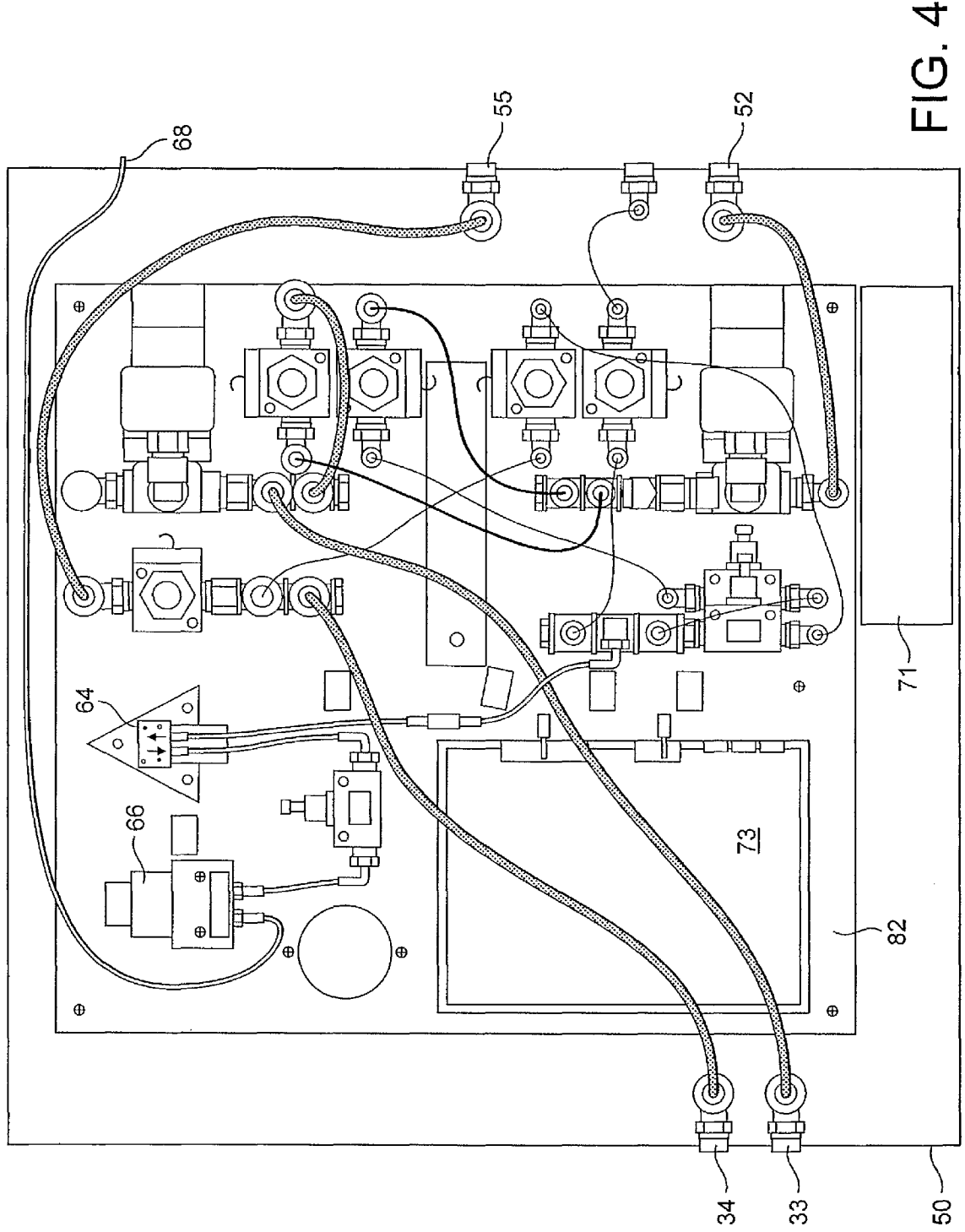
FIG. 4 is a layout diagram showing how the pneumatic circuitry shown in FIG. 3 may be incorporated on to a mounting board internally of the apparatus shown in FIG. 2.

The configuration of the various components internally of casing 50 is shown purely diagrammatically in FIG. 3. FIG. 4 is a diagrammatic view looking downwards towards the floor of the box-like casing of unit 30 showing how the relevant physical components are actually arranged in a typical layout.

Items identified in FIG. 3 with a reference number bear the same reference number in FIG. 4. What is more clearly shown in FIG. 4 is a base plate 82 on which all of the components are mounted save for the power supply 71 and the various ports and vents which are mounted in the front and rear walls of the box-like casing of unit 30.

The electronic circuitry on board 73 may be arranged to operate in a variety of ways depending on its on internal programming and on inputs from the buttons 75. In a preferred approach, the circuitry is programmed so that on powering up, there is brief self-test protocol which is carried out which checks the supply pressure of the gas supply connected to port 52 and that the relevant pressures are being achieved in various parts of the system under appropriate conditions. If there is a fault indication, this may be displayed on screen 39 enabling the operator to take appropriate action.

Oxygen sensors are themselves sensitive pieces of equipment and often need recalibration. The initial self-testing protocol may include such calibration, or calibration may be initiated at any time by the user.

The circuitry may also be set up to store a relevant parameter, for example, the oxygen detection level at which the purging of the interior of the container is judged to be sufficient. This may be adjusted by appropriate use of the buttons 75, which may have differing functions depending upon the programming of a control microprocessor on board 73, with the functions being indicated, for example, in customary fashion by an appropriate legend being displayed on the screen 39 by the side of each button 75.

Once the system has carried an appropriate self-testing protocol, and any error conditions attended to, for example, the purge gas supply not being connected to port 52, the unit may then indicate that it is ready to be used to purge a container. The operator may then connect a closed container to the ports 33 and 34 on the front of the unit 30 shown in FIG. 3 and press an appropriate button to initiate a cycle of purging until analysis of the gas coming out of container 32 shows that the oxygen level has dropped to that pre-set, at which point the gas ceases to be injected into the container and the pressure within the container is allowed to drop to the desired positive pressure for storage. The container can then be disconnected from the unit and a new one reconnected to be purged in similar fashion. The end of the process may be signalled by unit 30, for example, by an appropriate indication from LED 76 and/or by a message on graphic display 39 and/or by an audible signal from transducer 78.

The invention claimed is:

1. A system for storage of sensitive materials, comprising: a plurality of portable containers, wherein each portable container of which comprises a box with an inlet port and an exhaust port in a wall thereof, each of the inlet port and the exhaust port being a one-way valve or a check valve, and each portable container having means for sealing an interior of the box against outside of the box to provide a sealed enclosure preventing exchange of physical material between external surroundings of the container and contents of the container, and a container interior conditioning apparatus including means to inject an inert gas under pressure into one of the portable containers via the inlet port thereof, and means to analyze and monitor gas emerging from the exhaust port thereof during such injection, and further constructed and arranged to, on detection of a predetermined condition of the gas emerging from the container, discontinue injecting further inert gas via the inlet port.

2. The system according to claim 1, wherein the conditioning apparatus includes a gas analysis or detection system to monitor content of the gas emerging from the container.

3. The system according to claim 2, wherein the gas analysis or detection system is constructed and arranged to monitor oxygen content of the emerging gas and includes an oxygen sensor to detect oxygen concentration in the emerging gas.

4. The system according to claim 2, wherein the gas analysis or detection system is constructed and arranged to monitor moisture content of the emerging gas and includes a moisture sensor to detect concentration of water vapor in the emerging gas.

5. The system according to claim 1, including means to inject sufficient purge gas into the container to leave the container pressurized.

6. The system according to claim 2, including means to inject sufficient purge gas into the container to leave the container pressurized.

7. The system according to claim 3, including means to inject sufficient purge gas into the container to leave the container pressurized.

8. The system according to claim 4, including means to inject sufficient purge gas into the container to leave the container pressurized.

9. The system according to claim 1, including a manifold connecting the means to inject an inert gas to a plurality of inlets on a plurality of containers, and a manifold connecting the exhaust ports of the containers to the inlet port of the container interior conditioning apparatus.

10. A method of preserving sensitive materials which comprises placing the materials in a gas-impermeable container comprising a box with an inlet port and an exhaust port in a wall thereof, wherein each of the inlet port and the exhaust port are a one-way valve or a check valve, sealing an interior of the box against outside of the box to provide a sealed enclosure preventing exchange of physical material between external surroundings of the container and contents of the container, injecting a purge gas from a purge gas apparatus into the inlet port, monitoring a parameter of exhaust gas emerging during such injection from the exhaust port by means located in the purge gas apparatus, detecting when a value of the parameter has reached a predetermined level, and stopping injection of the purge gas once the predetermined level has been reached.

11. The method according to claim 10, wherein following the stopping of injection of the purge gas, pressure in the container is relieved to leave the container pressurized above ambient pressure.

* * * * *